United States Patent [19]
Kleesattel

[11] 3,958,450
[45] May 25, 1976

[54] RESONANT SENSING DEVICES AND METHODS FOR DETERMINING SURFACE PROPERTIES OF TEST PIECES

[76] Inventor: Claus Kleesattel, 9841-64th Road, Forest Hills, N.Y. 11374

[22] Filed: May 19, 1975

[21] Appl. No.: 578,946

[52] U.S. Cl. ............................ 73/67.2; 73/67.1; 73/81
[51] Int. Cl.² .................. G01N 3/48; G01N 29/00
[58] Field of Search ............... 73/67.1, 67.2, 78, 81

[56] References Cited
UNITED STATES PATENTS

| | | | |
|---|---|---|---|
| 3,153,338 | 10/1964 | Kleesattel | 73/67.1 |
| 3,572,097 | 3/1971 | Kleesattel | 73/67.1 |

*Primary Examiner*—Jerry W. Myracle
*Assistant Examiner*—John P. Beauchamp
*Attorney, Agent, or Firm*—Alvin Sinderbrand

[57] ABSTRACT

Surface properties, such as, hardness, of a test piece are determined by holding a mechanical resonator, for example, in the form of a sensor rod against a surface of the test piece with a static force sufficient to maintain steady contact with the test piece surface at a contact surface on the sensor rod shaped to provide an increasing area of contact with increasing plastic and/or elastic indentation or deformation of the test piece surface, exciting the test piece into vibration with a frequency which is varied so that the vibrations transmitted from the test piece to the sensor rod will cause the latter to attain a state of resonance, for example, as indicated when a maximum amplitude of the vibration of the sensor rod is sensed, measuring the amplitude of vibration of the excited test piece at a region of the latter which is adjacent to, but outside of the area of contact of the test piece with the contact surface on the sensor rod, for example, by means of an auxiliary sensor, and further varying the frequency of the vibratory excitation of the test piece in a range within which the sensor rod remains in the state of resonance to determine that frequency at which the measured amplitude of vibration of the test piece has a minimum value so that the difference between the frequency thus determined and the resonance frequency of the sensor rod when free of the test piece is an indication of the hardness or some other surface property of the test piece regardless of the mechanical reactance of the latter.

22 Claims, 14 Drawing Figures

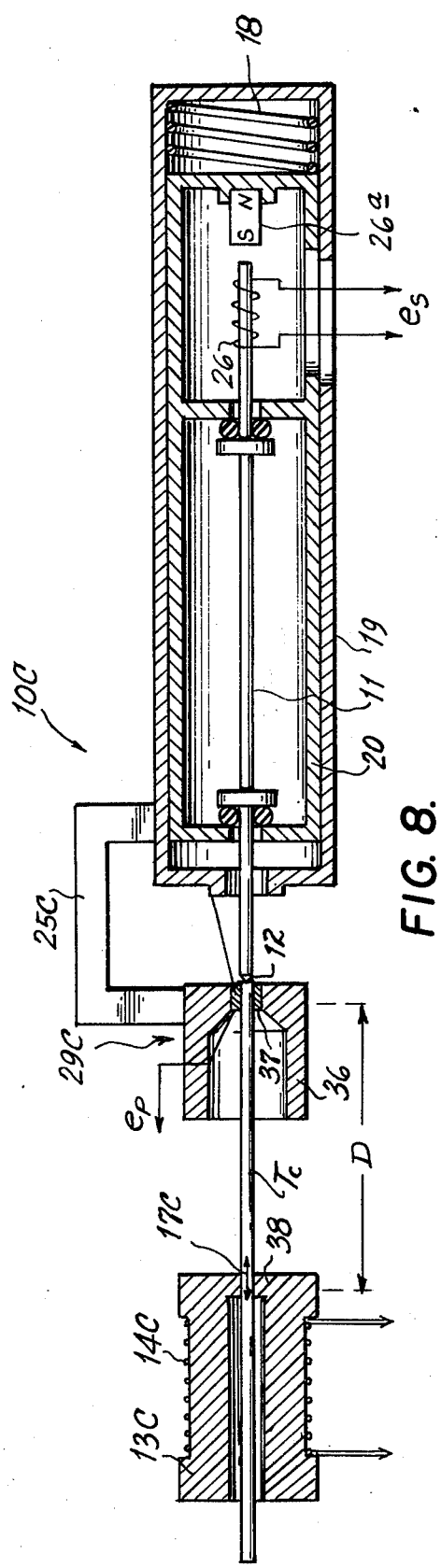
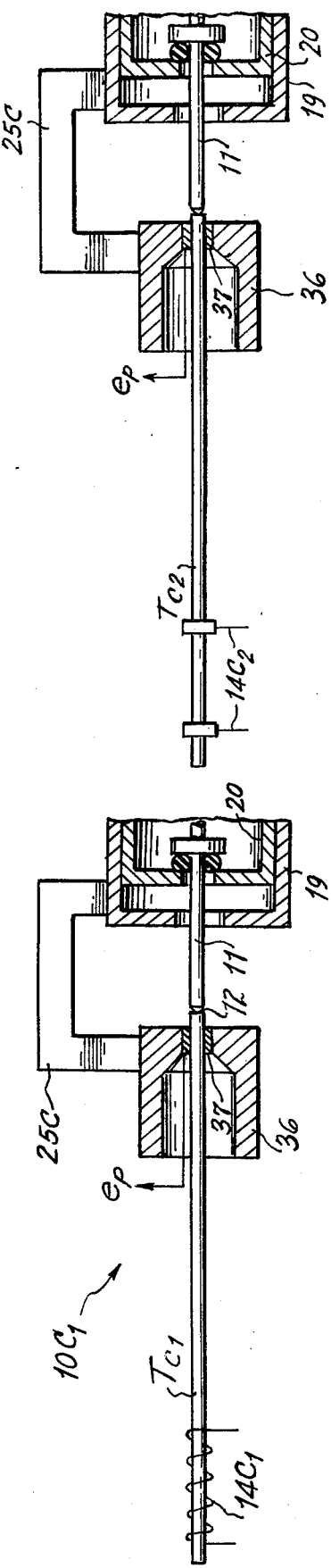
FIG. 8.
FIG. 9.
FIG. 10.

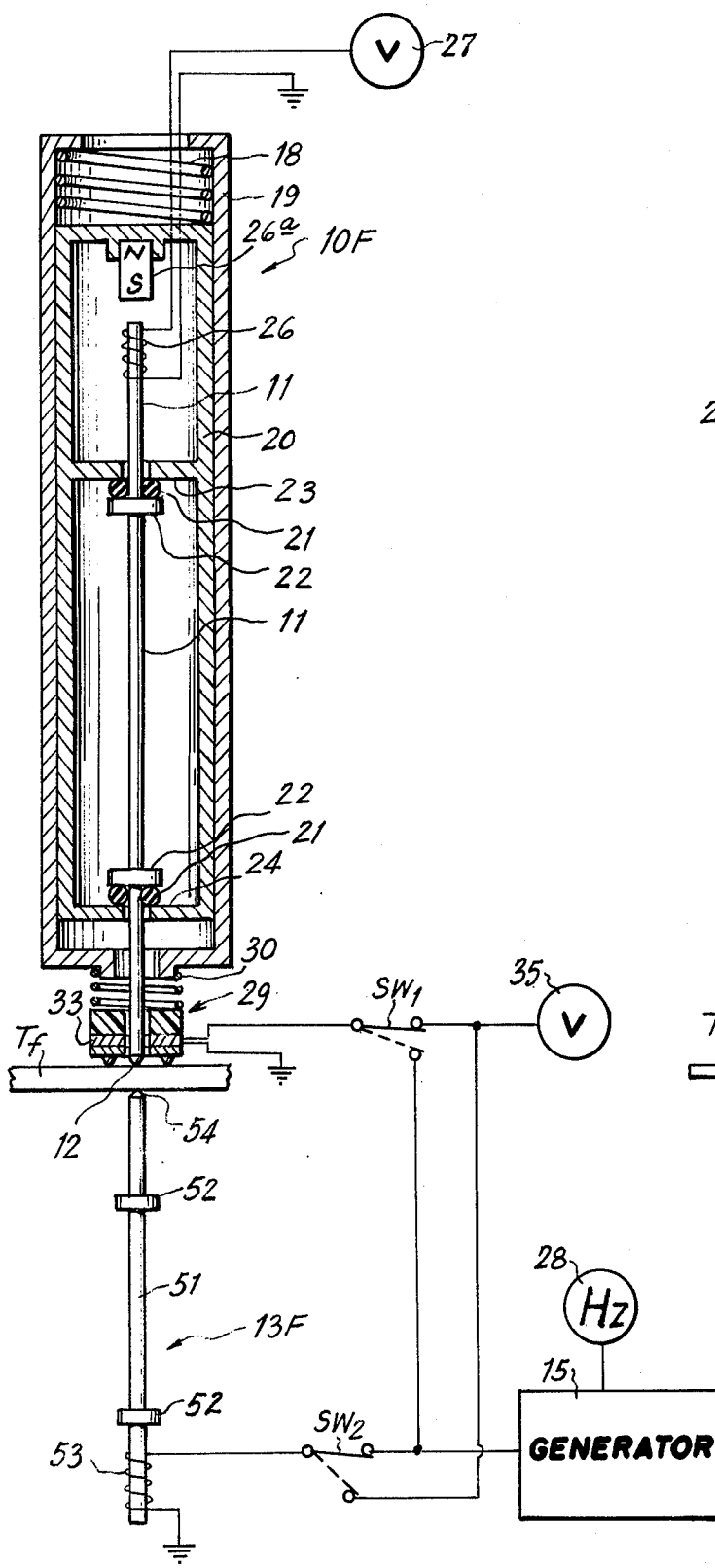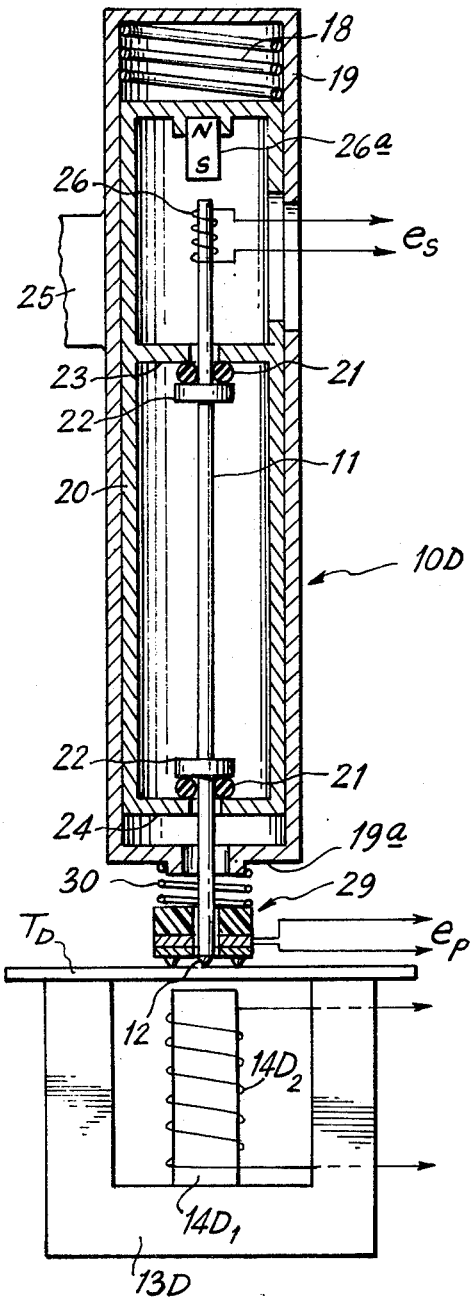

RESONANT SENSING DEVICES AND METHODS FOR DETERMINING SURFACE PROPERTIES OF TEST PIECES

BACKGROUND OF THE INVENTION

1. Field of the Invention

This invention relates generally to resonant sensing devices and methods which can be used to determine or test the physical properties or characteristics of a test piece or solid particularly at the surface of the latter.

2. Description of the Prior Art

It is known, for example, as disclosed in my U.S. Pat. No. 3,153,338, issued Oct. 20, 1964, to provide a resonant sensing device for indicating the surface properties, for example, hardness, of a test piece. Such known device comprises a mechanical resonating means or sensor having a hemispherical, conical, pyramidal or otherwise shaped contact surface to afford contact with a test piece over progressively increasing areas with increasing penetration or indentation of a surface of the test piece by the contact surface of the mechanical resonating means, electrically energized means for effecting vibration of the mechanical resonating means at a resonance frequency of the latter, and means exerting a static force for holding the contact surface of the vibrated mechanical resonating means in steady contact with the test piece so as to cause plastic and/or elastic indentation or deformation of the surface of the latter to an extent dependent upon the surface characteristics of the test piece and the magnitude of the static force. Two basic methods of operating the above described device have been proposed.

In one of these methods of operation, a constant static force is used for maintaining the steady contact and a tunable generator is used for effecting vibration of the resonating means. When the resonance frequency of the mechanical resonating means is altered from the resonance frequency in its free state by reason of its steady contact with the test piece, the generator frequency is varied until resonance is restored, and such variation of the generator frequency is measured as an indication of the surface characteristics, for example, the hardness of the test piece.

In another method of operating the described device, the frequency at which the mechanical resonating means is vibrated is fixed at a value different from the resonance frequency of the mechanical resonating means when in the free state or condition, and the static force by which the mechanical resonating means is held in steady contact with the test piece is progressively increased until resonance is achieved. In this method of operation, the magnitude of the static contact force required to produce resonance is measured as an indication of the surface characteristics of the test piece.

It has further been known, for example, as disclosed in my U.S. Pat. No. 3,572,097, issued Mar. 23, 1971, to operate a resonant sensing device, as aforesaid, with both the generator frequency and the static contact force being fixed, and with any variation of the resonance frequency of the mechanical resonating means resulting from its contact with the test piece being cancelled or reversed by varying the free resonance frequency of the resonating means, that is, by varying a characteristic or parameter of the mechanical resonating means which determines its resonance frequency, whereupon, such variation of the characteristic or parameter is measured as an indication of the surface properties of the test piece. Among the resonance frequency determining characteristics or parameters of the mechanical resonating means that may be varied are an elastic modulus thereof, as by varying a magnetic polarizing field in the case where the mechanical resonating means includes a magnetostrictive rod or an electric polarizing field in the case where the mechanical resonating means includes an electrostrictive or piezo-electric rod, or by varying the temperature of the mechanical resonating means. Further, where the mechanical resonating means includes an electromechanical transducer, its varied characteristic or parameter may be the coupling thereof to electrical circuits by which the transducer is energized from the fixed or constant frequency generator. The varied characteristic or parameter of the mechanical resonating means which determines its resonance frequency may also be its shape, mass distribution relative to its nodes and loops of vibration, or a force other than the static contact force which is applied to the mechanical resonating means remote from its contact surface to add elastic strain energy.

Although some of the above described resonant sensing devices and methods of operating the same have enjoyed widespread commercial success, it has been found that, under certain conditions, appreciable errors arise in the measurements of the hardness or other surface properties obtained thereby. More particularly, in the theoretical basis for the existing resonant sensing devices, it has been assumed that the mechanical reactance of the test piece is infinitely large or at least very much larger than the contact reactance. This assumption is reasonable in many cases, for example, when the test piece is relatively large and/or massive or, in the case of a relatively small test piece, when such test piece can be adequately clamped or mounted, for example, by grease-coupling of the test piece to a heavy base such as a steel block, so that the resulting measuring error is then within acceptable limits. However, when flexural waves are excited in the test piece, as may happen when the test piece is very small or thin or is thin-walled and hollow and thus cannot be supported at the surface opposed to that engaged by the contact surface of the resonating means, the error which results from the reactance of the test piece may not be negligible. A similar problem may arise, even with a test piece of substantial size or mass, if a large static force, for example, of the order of 100 kg., is employed for holding the contact surface of the vibrated mechanical resonating means in steady contact with the test piece.

OBJECTS AND SUMMARY OF THE INVENTION

Accordingly, it is an object of this invention to provide resonant sensing devices and methods which can be used to accurately determine or test the surface properties, such as, hardness, of a test piece regardless of the mechanical reactance of the latter.

In accordance with an aspect of this invention, the surface properties of a test piece are determined by holding a mechanical resonating means, such as, a sensor rod, against a surface of the test piece with a static force sufficient to maintain steady contact with the test piece at a contact surface on the sensor rod shaped to provide an increasing area of contact with increasing indentation or deformation of the test piece surface by the shaped contact surface, exciting the test piece into vibration with a frequency which is varied so that the vibrations transmitted from the test piece to the sensor rod will cause the latter to attain a state of resonance in dependence on the mechanical coupling between the sensor rod and test piece at the area of contact therebetween, measuring the amplitude of vibration of the vibrated test piece at a region of the latter which is adjacent to, but outside of the area of contact of the test piece with the contact surface on the sensor rod, for example, by means of an auxiliary sensor, and further varying the frequency of the vibratory excitation of the test piece in a range within which the sensor rod remains in the state of resonance thereof to determine that frequency at which the measured or detected amplitude of vibration of the test piece has a minimum value so that the difference between the frequency that is thus determined and the resonance frequency of the sensor rod in its free state, that is, when free of the test piece, is an indication of the surface properties, for example, the hardness, of the test piece regardless of the mechanical reactance of the latter.

The above, and other objects, features and advantages of the invention, will be apparent in the following detailed description of illustrative embodiments thereof which is to be read in connection with the accompanying drawings.

BRIEF DESCRIPTION OF THE DRAWINGS

FIG. 5 is a schematic, axial sectional view of a resonant sensing device according to another embodiment of this invention and which is particularly suited for indicating the surface properties of plate-like test pieces of small thickness, such as, razor-blades and the like;

FIG. 8 is a schematic axial sectional view of a resonant sensing device according to still another embodiment of the invention and which is particularly suited for indicating the surface properties of elongated rod- or wire-shaped test pieces;

FIGS. 9 and 10 are schematic views similar to portions of FIG. 8, but showing resonant sensing devices according to this invention for use with test pieces which are of magnetostrictive and electrostrictive materials, respectively;

FIG. 11 is a view similar to that of FIG. 1, but showing a resonant sensing device for use with ferromagnetic test pieces;

FIG. 13 is a schematic axial sectional view of a resonant sensing device according to yet another embodiment of this invention.

DESCRIPTION OF THE PREFERRED EMBODIMENTS

Figure 1:
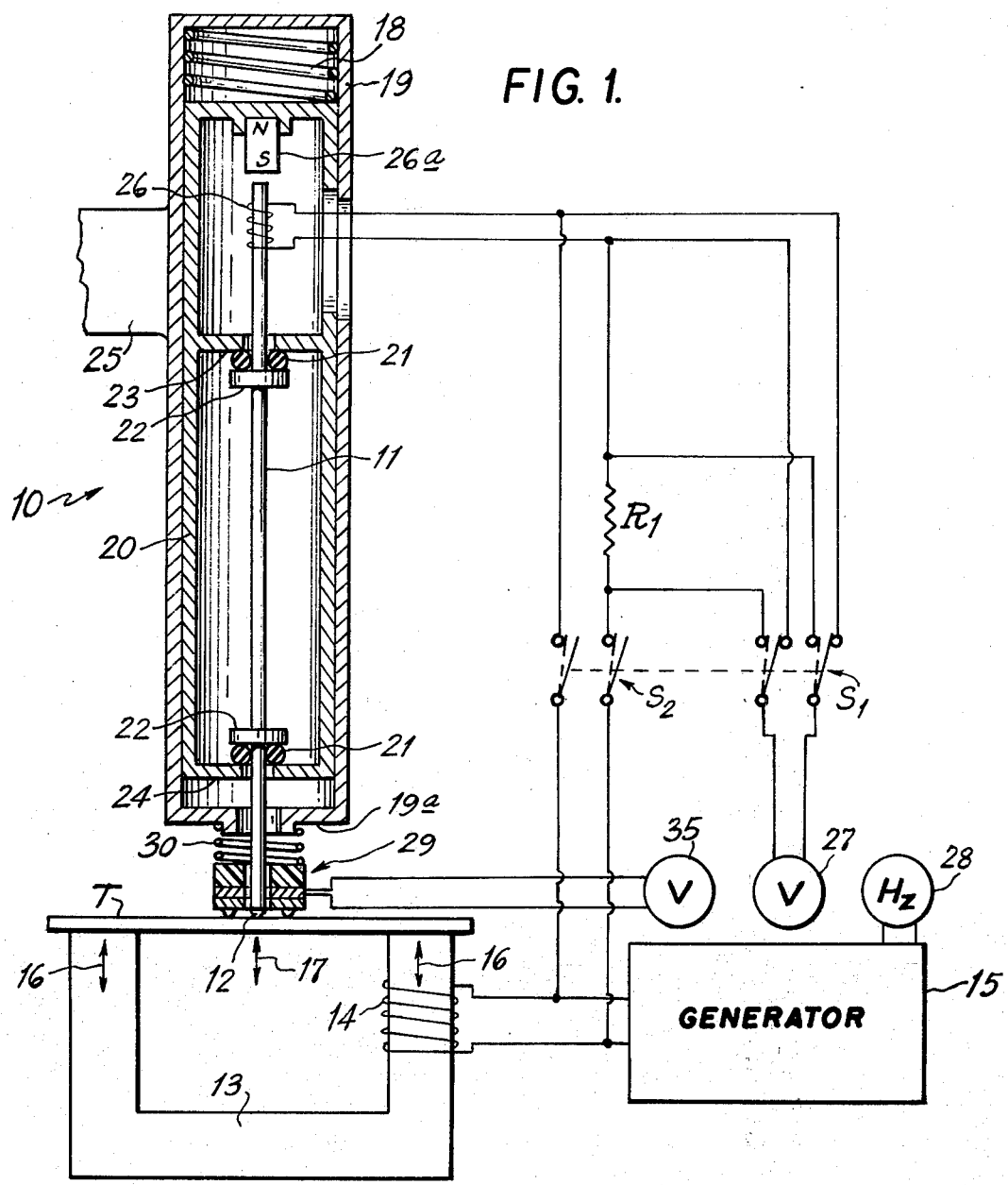
FIG. 1 is a schematic, axial sectional view of a resonant sensing device according to one embodiment of this invention for indicating the surface properties of a test piece.

Before proceeding with a detailed description of the resonant sensing devices and methods according to this invention, further consideration will be given to the problems inherent in the above described existing devices, for example, as disclosed in U.S. Pat. No. 3,153,338. As previously noted, in such existing devices, a mechanical resonating means, for example, in the form of a sensor rod, is provided with a contact surface which is pressed against a surface of the test piece with a static force sufficient to maintain steady contact therebetween and which is shaped to provide increasing areas of contact with increasing indentation of the test piece surface by the shaped contact surface of the sensor rod. Thus, the indentation of the test piece surface, and hence the area of contact of the sensor rod with the test piece, are dependent upon the surface characteristics, for example the hardness, of the test piece and the magnitude of the static force. Further, in such existing devices, electrically energized means are provided for effecting vibration of the sensor rod at a resonance frequency of the latter. In the case, for example, where a constant static force is used for maintaining the steady contact of the contact surface of the sensor rod with a surface of the test piece, a tunable generator is used for effecting vibration of the sensor rod. When the resonance frequency of the sensor rod is changed from the resonance frequency thereof in its free state by reason of the steady contact or mechanical coupling of the sensor rod with the test piece, the generator frequency is varied until the sensor rod is again in the state of resonance, and such variation of the generator frequency is measured as an indication of the hardness or other surface characteristics of the test piece.

In explaining the theoretical basis for the indication of hardness resulting from the foregoing, the resonance equation for the sensor rod when mechanically coupled to the test piece has been given as follows:

$$\alpha \tan \alpha = L/ES\ K \qquad (1)$$

in which $L$, $S$ and $E$ are the length, cross-sectional area and elastic modulus, respectively, of the sensor rod, and $K$ is the elastic stiffness of the contact to be measured, and which is derived from the fact that a spring of stiffness $K$ can be substituted for the mechanical coupling between the sensor rod and the test piece. Further, in equation (1), $$\alpha = \frac{2\pi fL}{c} = \frac{\omega L}{c} \qquad (2)$$

in which $c$ is the velocity of sound in the material of the sensor rod, and $f$ is the resonance frequency of the sensor rod. Since $K^2$ is proportional to the area of contact of the sensor rod with the test piece surface for the case where the vibration of the sensor rod is generally normal to such surface, and since the area of contact is dependent upon the hardness of the test piece, as indicated above, equation (1) has been considered a basis for determining hardness of the test piece from the change in the resonance frequency of the vibrated sensor rod.

In deriving equation (1), it has been assumed that the mechanical reactance of the test piece is infinitely large. A more general derivation of the resonance equation yields $$\alpha \tan \alpha = \frac{\frac{L}{ES} K}{1 - \frac{K}{\omega X_p}} \qquad (3)$$

in which $X_p$ is the mechanical reactance of the test piece and $\omega$ is again $2\pi f$. It will be seen that equation (3) reduces to equation (1) when $X_p$ approaches infinity. In many testing situations, the error term $K/\omega X_p$ is very much smaller than unity and is therefore negligible. It can be shown that this is principally the case when only longitudinal waves appear in the test piece. However, when flexural waves become predominant in the test piece, that error term may become substantial so that it cannot be neglected if the measuring error is to be maintained within acceptable limits.

In accordance with the present invention, the influence of the mechanical reactance of the test piece on the accuracy of the hardness measurement is eliminated by effecting vibratory excitation of the test piece, rather than of the mechanical resonating means or sensor rod, and by varying the frequency of excitation of the test piece so that the sensor rod attains a state of resonance in dependence on its mechanical coupling to the test piece, whereupon the frequency of excitation of the test piece is further varied in a range in which the sensor rod remains in the state of resonance to determine that frequency at which a minimum amplitude of vibration of the test piece is achieved in a region of the latter near to the area of contact of the sensor rod with the test piece. It has been found that the difference between the frequency as thus determined and the resonance frequency of the sensor rod in its free state, that is, when not in contact with the test piece, is an accurate indication of the surface properties, for example, the hardness, of the test piece regardless of the mechanical reactance of the latter. It will be appreciated that, when the test piece is excited into vibration, the sensor rod functions like a dynamic damper. Thus, in the state of resonance of the sensor rod, the latter strongly depresses the amplitude of vibration of the test piece at and near to the area of contact of the latter with the shaped contact surface of the sensor rod. The frequency of vibration which produces the state of resonance of the sensor rod and also the minimum amplitude of vibration of the test piece near to the area of contact can be shown to be equal to the resonance frequency of the sensor rod that would be measured if the mechanical reactance of the test piece was infinitely large. Consequently, possible errors owing to the size of the test piece or to other test conditions are eliminated.

More specifically, when the sensor rod is held in contact with the test piece which is excited into vibration, the reactance of the sensor rod, including the contact reactance, is given by the following equation:

$$X_{KS} = \frac{\frac{ES}{c} \tan \alpha}{1 - \frac{ES}{LK} \alpha \tan \alpha} \qquad (4)$$

in which $L$, $S$, $E$, $K$, $c$ and $\alpha$ all have the meanings indicated above. The exciting frequency at which the resonance $X_{KS}$ attains its maximum value occurs when the amplitude of vibration of the test piece near to the area of its contact with the sensor rod is a minimum value or approaches zero, or even more precisely when the ratio of such amplitude of vibration of the test piece to the amplitude of vibration of the sensor rod is a minimum value or approaches zero. By using the approach to zero of such ratio of the amplitudes of vibration of the test piece and sensor rod, respectively, for determining the exciting frequency providing the maximum value of $X_{KS}$, one avoids the possibility of erroneously determining an exciting frequency which does not correspond to the state of resonance of the sensor rod but at which a node of vibration, usually a node of flexural vibration, forms at the location where the amplitude of vibration of the test piece is being measured or detected so that such measured amplitude nears zero. For a similar reason, one cannot just rely on the measurement of the maximum amplitude of vibration of the sensor rod for, due to structural resonances in the test piece, or in the combination of the test piece and exciter therefor, maximum amplitudes of vibration of the sensor rod may appear at frequencies other than the one at which the sensor rod functions as a dynamic damper. For the excitation frequency at which the ratio of the amplitudes of vibration of the test piece and sensor rod, respectively, is a minimum value or approaches zero, the value of $X_{KS}=\infty$ (that is, the state of resonance of the sensor rod), and this occurs when $$\frac{ES}{L} \alpha \tan \alpha = K \qquad (5)$$

is substituted in equation (4). It will be seen that the condition of equation (5) for establishing $X_{KS}=\infty$ in equation (4) is identical with the resonance equation (1). Thus, the correct value for $K$ is obtained as if the reactance $X_p$ of the test piece was infinitely large, that is, the value of $K$ is found regardless of the actual reactance of the test piece.

Theoretically, the amplitude of vibrations of the test piece at the area of contact with the contact surface on the sensor rod should approach zero when the sensor rod is in a state of resonance. Due to the ever present damping, the minimum amplitude of such vibration of the test piece is always somewhat greater than zero. However, as the test piece is reduced in size or mass or becomes more flexible, the minimum amplitude of vibration of the test piece becomes more pronounced, whereas the state of resonance of the sensor rod occurs over a relatively wider band of frequencies. In practicing the method according to this invention, conventional means may be employed for detecting or indicating the vibrational amplitudes of the sensor rod and test piece, respectively, for example, by converting the vibrational displacements of the sensor rod and test piece into respective AC voltages which can be indicated by suitable meters. Thus, with the shaped contact surface of the sensor rod being held in steady contact with a surface of the vibrated test piece, the frequency of the vibratory excitation of the test piece may be varied to seek that frequency at which the meter showing the voltage corresponding to the amplitude of vibration of the test piece near to the area of contact with the sensor rod indicates a minimum value, while making sure, through observation of the meter corresponding to the amplitude of vibration of the sensor rod, that the frequency thus determined does not coincide with a minimum value of the vibration amplitude of the sensor rod. The difference between the frequency thus determined and the previously determined resonance frequency of the sensor rod in its free state will indicate the hardness or other surface properties of the test piece. Alternatively, it is preferred that the ratio of the voltages corresponding to the amplitudes of vibration of the test piece and sensor rod, respectively, be established, and the frequency of vibratory excitation of the test piece be tuned either manually or automatically to the frequency at which such ratio has a minimum value, that is, the frequency at which the amplitude of vibration of the test piece has a minimum value while the sensor rod is in a state of resonance and, therefore, does not simultaneously show a minimum or low amplitude of vibration. Of course, the foregoing may be achieved by establishing the ratio of the voltages corresponding to the amplitudes of vibration of the sensor rod and test piece, respectively, and then tuning for the maximum value of such ratio.

As a matter of fact, the amplitude of vibration of the test piece approaches zero only at the area of contact thereof with the sensor rod. Therefore, the amplitude of vibration of the test piece should be detected or sensed as close as possible to such area of contact. In practice, it is advantageous to detect or sense the amplitude of vibration of the test piece at a location which is spaced from the area of contact with the sensor rod by a distance no greater than $\lambda/4$, where $\lambda$ is the wavelength of the wave generated in the test piece by the vibratory excitation thereof. However, the location at which the amplitude of vibration of the test piece is detected or sensed must not be included in the area of contact of the test piece with the sensor rod, as that would alter the reactance equation (4). In order to ensure that the reactance equation (4) will be applicable, it is desirable that the distance from the center of the area of contact to the location at which the amplitude of vibration of the test piece is detected or sensed should be at least ten times the mean radius of the area of contact. In the case where such area is circular, the mean radius is the actual radius of the area of contact. However, where the area of contact is not circular, for example, in the case of a square area of contact as is achieved with a Vickers indent, the mean radius is approximately 0.4 times the diagonal dimension of the square area.

In the case where the mechanical resonating means is in the form of an elongated sensor rod which is advantageously vibrated longitudinally by reason of the engagement of the contact surface at an end of the rod with a surface of the vibrated test piece, the sensor rod is preferably disposed with its longitudinal axis extending normal or perpendicular to the test piece surface at the area of contact with the latter, and the test piece is preferably excited in such a way that, at least in the vicinity of such area of contact, the vibration of the test piece has a substantial component normal to the test surface, that is, in the direction of the longitudinal axis of the sensor rod. When the sensor rod is in a state of resonance, it is the component of the vibration of the test piece in the direction of the sensor rod axis which is sensed or detected at the region near to the area of contact for determining the frequency at which the amplitude of such vibration nears zero. Of course, the vibrations transmitted to the sensor rod or other mechanical resonating means from the vibrated test piece may be flexural, transversal, radial or torsional, rather than longitudinal as described above.

It is an advantageous characteristic of the present invention that the vibrations with which the test piece is excited need not have frequencies in the ultrasonic range, that is, vibration frequencies in any suitable range, including frequencies well below the ultrasonic range, may be employed. This is to be distinguished from the previously known resonant sensing devices, for example, of the type disclosed in U.S. Pat. No. 3,153,338, in which relatively higher, preferably ultrasonic frequencies are required for the purpose of minimizing the error term $K/\omega X_p$ in the denominator of the resonance equation (3).

Referring now to FIG. 1 of the drawings, it will be seen that a sensing device embodying the present invention and there generally identified by the reference numeral 10 comprises mechanical resonating means shown to include a sensor in the form of an elongated rod 11 having a tip 12 at one end of diamond or other suitably hard material. Such tip 12 provides a contact surface which is shaped so that, when the tip is urged against a test piece T, a defined area of contact of tip 12 with the surface of test piece T is formed, with the size of such area of contact increasing progressively with increasing indentation or deformation of the test piece surface. Thus, the tip 12 may be of hemispherical, conical, pyramidal or other configuration for achieving the foregoing relationship of area of contact to extent of surface deformation or indentation.

The device 10 of FIG. 1 is intended for use with a plate-like test piece of various thicknesses which is supported on a generally C-shaped anvil 13 of magnetostrictive material having a winding 14 thereon which receives electrical oscillations from a generator 15. The generator 15 is suitably controllable to vary the frequency of the electrical oscillations supplied to winding 14, and of the resulting vibrations produced in anvil 13. The anvil 13 is shaped and dimensioned so that the vibrations generated therein at the ends of its legs on which the test piece T is supported will be in the directions indicated by the arrows 16, that is, perpendicular or normal to the surfaces of the plate-like test piece, and so that the resulting vibratory excitation of test piece T will cause vibrational displacements of the latter perpendicular to the surfaces of the test piece at the portion of the latter intermediate the legs of anvil 13, for example, as indicated by the arrow 17.

It will be apparent that, when the tip 12 of sensor rod 11 is pressed against the surface of test piece T at the portion of the latter intermediate the legs of anvil 13 with the axis of rod 11 extending perpendicular to the test piece surface, as shown, vibrational energy is transmitted to rod 11 from test piece T at the area of contact therebetween so as to cause longitudinal vibration of the sensor rod.

The sensor rod 11 may be dimensioned so that nodes of its longitudinal vibrational movement occur intermediate its ends. This condition is approximately satisfied by providing rod 11 with a length that is a whole multiple of the wavelength of the compressional waves generated in the material of the sensor rod at the frequency of the vibrational excitation of the test piece.

The tip 12 may be conveniently held in steady contact with test piece T, that is, without separating from the latter or tapping as a result of the vibration of the test piece, by a static force acting longitudinally on rod 11 in the direction toward its tip 12. As shown, such static force may be applied by a compression spring 18 acting between an outer housing 19 and an inner sleeve 20 which is slidable in the latter. The rod 11 is shown to be mounted within sleeve 20 by means of rubber rings 21 seating against opposite faces of two radial flanges 22 provided on rod 11 at nodes of longitudinal vibrational movement of such rod and being respectively constrained by an inwardly directed radial flange 23 in sleeve 20 and by the lower end wall 24 of the latter. The end of rod 11 carrying tip 12 projects axially from the lower end of sleeve 20. The outer housing 19 may be suitably supported, as indicated schematically at 25, so as to be fixed relative to the vibrational exciting anvil 13. It will be apparent that, with the foregoing arrangement, the spring 18 determines the magnitude of the static force with which tip 12 of sensor 11 is held in steady contact with test piece T while the latter is supported on, and vibrationally excited by anvil 13.

In order to determine when sensor rod 11 is in a state of resonance as a result of the vibrational energy transmitted thereto from the vibrated test piece T at the area of contact of the latter with tip 12, the sensor rod 11 may be formed of a magnetostrictve material, for example, nickel, permanickel, permendur, the alloy known as Ni-Span-C (which contains 42% nickel, 5% chromium and 2% titanium and the balance being substantially iron), or other metals which have reasonably small band widths (high mechanical Q), and a pickup coil or winding 26 extends around the end portion of sensor rod 11 remote from tip 12 so that, in the presence of a polarizing magnetic field, for example, from a permanent magnet 26a, an alternating voltage will be induced in coil 26 in response to longitudinal vibration of the sensor rod. A vacuum tube or other voltmeter 27 may be connected to pickup coil 26 to indicate the magnitude of the voltage induced in the pickup coil, and hence the amplitude of the vibrations of rod 11, which vibrations have maximum amplitudes when either the sensor rod or the test piece is in a state of resonance. The electrical oscillation generator 15 may be manually tunable to vary the frequency of the electrical oscillations supplied to winding 14 within a suitable range of frequencies, and a conventional frequency meter 28 is connected with generator 15 to indicate the frequency of the oscillations generated by the latter.

Figure 3:
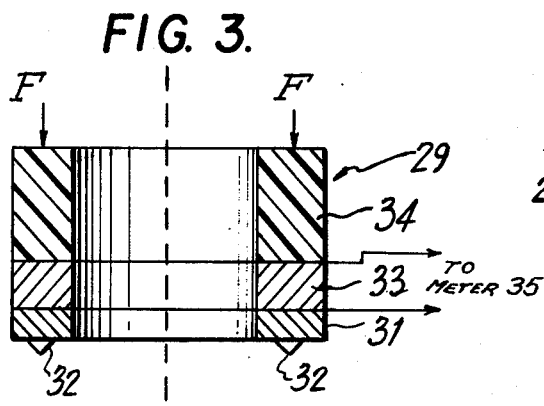
FIG. 3 is an enlarged axial sectional view of the element in the device of FIG. 1 for detecting or sensing the amplitude of vibration of the test piece.
Figure 4:
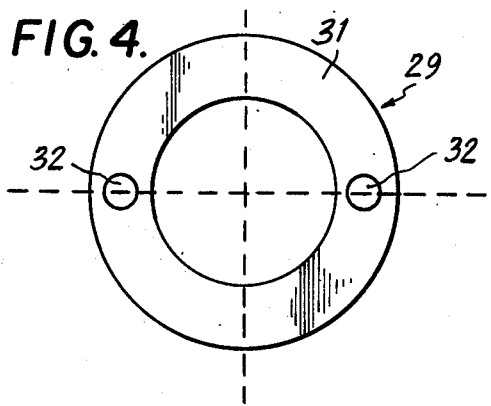
FIG. 4 is a bottom plan view of the element of FIG. 3.

In accordance with this invention, the resonant sensing device 10 further includes an auxiliary sensor 29 for sensing or detecting the amplitude of the vibrations of test piece T near to the area of contact of the latter with tip 12 of the sensor rod. In the embodiment of FIG. 1, the auxiliary sensor 29 is shown to be of annular configuration and to extend around the lower end portion of sensor rod 11, and a coil spring 30 is interposed between the lower end wall 19a of outer housing 19 and auxiliary sensor 29 for urging the latter against the same surface of test piece T as is contacted by tip 12. As shown particularly on FIGS. 3 and 4, the auxiliary sensor 29 may be comprised of a metal ring 31 having two or more suitably hard contact points 32 depending therefrom and being equally spaced apart about ring 31, a ring 33 of electrostrictive or piezoelectric material bonded to the upper surface of ring 31, and an upper insulating ring 34 bonded to the upper surface of piezoelectric ring 33 to receive the thrust of spring 30 indicated by the arrows F on FIG. 3. It will be apparent that, when tip 12 of sensor rod 11 is urged by spring 18 into contact with a surface of test piece T on exciting anvil 13, spring 30 is effective to urge contact points 32 into contact with the same surface of the test piece near to the area of contact of the latter with tip 12. Thus, when the test piece T is vibrationally excited by anvil 13 and vibrational energy is transmitted to rod 11 at the area of contact of tip 12 with the test piece, the vibrations of the test piece near to that area of contact are also transmitted through contact points 32 and ring 31 to the piezoelectric ring 33 so that the latter produces a voltage which is indicated by a voltmeter 35 suitably connected to ring 33, and which is of a magnitude dependent on the amplitude of the vibrations of the test piece at the locations engaged by points 32. If desired, the contact points 32 can be omitted and ring 31 can be grease-coupled to the test piece, as by a layer of mineral oil or grease interposed therebetween.

In operating the above described resonant sensing device 10 with the tip 12 of sensor rod 11 pressed against a surface of test piece T supported on anvil 13, the generator 14 is tuned or adjusted until the reading on voltmeter 35 is zero or at least a minimum value, thereby indicating that the amplitude of vibration of the test piece near to the area of contact of the latter with tip 12 has approached zero or at least is a minimum value. During such tuning or adjustment of generator 15 to attain a minimum or zero reading on voltmeter 35, voltmeter 27 is observed to make sure that the latter does not show a minimum valve of the vibration amplitude of the sensor rod 11 simultaneously with the display of the minimum value of the vibration amplitude of test piece T by the meter 35. Frequency meter 28 is read to indicate the frequency at which meter 35 shows a zero or minimum amplitude of vibration of test piece T near to the area of contact with tip 12 while meter 27 continues to show a state of resonance of sensor rod 11. The difference between such frequency reading on meter 28 and the resonance frequency of sensor rod 11 in its free state, that is, when removed from contact with test piece T, is then a measure of the surface properties, for example, hardness, of the rest piece T.

In order to permit the resonance frequency of sensor rod 11 in its free state to be predetermined, a technique disclosed in U.S. Pat. No. 3,153,338 may be employed. More specifically, as shown on FIG. 1, a switch $S_1$ may be provided to connect meter 27 directly with pickup coil 26 when switch $S_1$ is in the position shown in full lines, and to connect meter 27 across a resistance $R_1$ when switch $S_1$ is changed over to the position shown in broken lines. Further, a switch $S_2$ is ganged with switch $S_1$ and connects pickup coil 26 in series with resistance $R_1$ to the output of generator 15 when switch $S_2$ is changed over from the position shown in full lines to the position shown in broken lines.

The switches $S_1$ and $S_2$ are changed over from their positions shown in full lines to the positions shown in broken lines only for determining the resonance frequency of sensor rod 11 in its free state. With switches $S_1$ and $S_2$ thus changed over, the electrical oscillations from generator 15 are applied to coil 26 which thereby functions to excite longitudinal vibrations in rod 11 while the latter is out of contact with any test piece. As the frequency of the oscillations generated by generator 15 is varied, there is a sudden change in the impedance of coil 26 which results in a corresponding sudden change in the voltage drop across resistance $R_1$, as indicated by meter 27, so that the occurrence of the sudden voltage change shown by meter 27 is an indication that the generator 15 has been tuned to the resonance frequency of the rod 11 in its free state and this frequency can be read on meter 28.

Alternatively, the surface properties or hardness of the test piece T may be determined by the difference between the frequency read on the meter 28 when voltmeter 35 indicates the zero or minimum amplitude of vibration of the test piece near to its area of contact with tip 12 while meter 27 indicates the state of resonance of sensor rod 11, and the similar frequency reading obtained on meter 28 when tip 12 of the sensor rod is in contact with a test piece of known surface properties or hardness.

Figure 2:
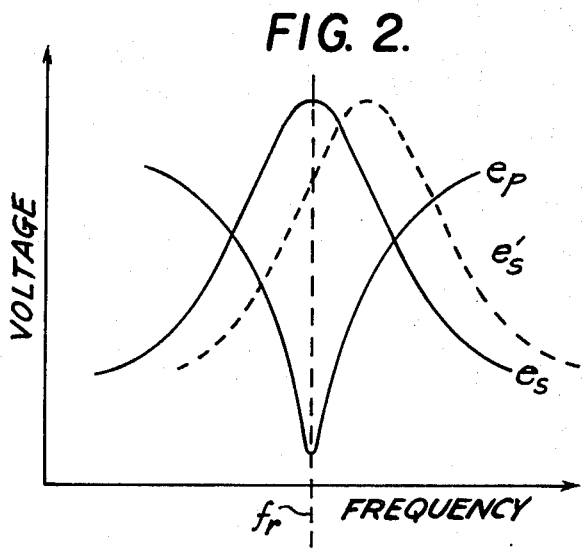
FIG. 2 is a graphical representation of the relationship between the outputs of elements which detect the amplitudes of vibration of the test piece and of a sensor rod, respectively, during operation of the device of FIG. 1.

Referring to FIG. 2 in which the curves $e_p$ and $e_s$ represent the output voltages of the piezoelectric ring or element 33 of auxiliary sensor 29 and of the pickup coil 26 on sensor rod 11, respectively, in a range of frequencies near to the resonance frequency of sensor rod 11, it will be seen that, particularly in the case of experiments conducted with test pieces that are small or flexible, the minimum value of the curve $e_p$ has appeared to be more sharply defined than the maximum value of the curve $e_s$. Under certain testing conditions, usually due to a lack of symmetry, the maximum of the output voltage from pickup coil 26, as indicated by the curve $e'_s$ in broken lines on FIG. 2, may occur at a frequency that is slightly different from the frequency $f_r$ which results in the minimum output voltage from auxiliary sensor 29. However, the foregoing does not affect the accuracy of the measurement of the surface properties or hardness of the test piece, as the frequency $f_r$ for determining such surface properties or hardness in accordance with this invention is always that at which the minimum output voltage from the auxiliary sensor is obtained. Thus, the pickup coil 26 and associated voltmeter 27 are provided merely for ensuring that, at the frequency of vibrational excitement of the test piece providing a minimum reading of output voltage on meter 35, the sensor rod 11 is in a state of resonance indicated by a relatively large voltage reading on meter 27.

Figure 1A:
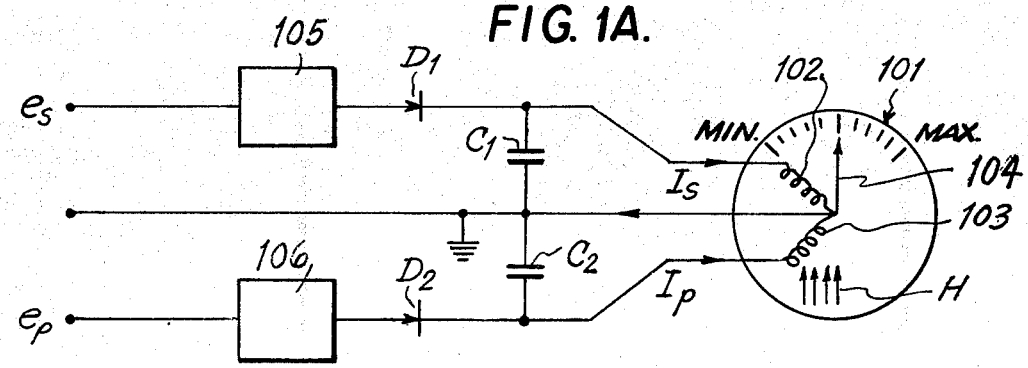
FIG. 1A is a wiring diagram showing a preferred circuit arrangement for use with a resonant sensing device according to this invention.

Referring now to FIG. 1A, it will be seen that, in a preferred circuit arrangement for determining the frequency $f_r$ at which the amplitude of vibration of the test piece near to its area of contact with the sensor rod 11 has a minimum value while the sensor rod is in a state of resonance and thus has a relatively large amplitude of vibration, the voltmeters 27 and 35 of FIG. 1 are replaced by a so-called quotient-forming meter 101. The meter 101 is shown to have a crossed-coil movement made up of orthogonally related coils 102 and 103 connected with a pointer 104 and disposed in a permanent magnetic flux H, for example, from a permanent magnet. The output voltage $e_s$ from pickup coil 26 is applied to an amplifier 105 which has its output connected through a rectifying diode $D_1$ to one end of coil 102, while the opposite end of coil 102 is connected to ground and a capacitor $C_1$ is connected across coil 102. Similarly, the output voltage $e_p$ of auxiliary sensor 29 is applied to an amplifier 106 having its output connected through a rectifying diode $D_2$ to one end of coil 103 which has its opposite end connected to ground with a capacitor $C_2$ connected across coil 103.

With the quotient-forming meter 101 connected as shown on FIG. 1A, decreasing $e_p$ toward zero, that is, decreasing the current $I_p$ in coil 103, causes the crossed-coil movement to turn in the direction moving coil 102 toward the horizontal, as viewed on the drawing, so that pointer 104 moves toward the "minimum" end of the associated scale. Conversely, decreasing $e_s$ toward zero, that is, decreasing the current $I_s$ in coil 102, causes the crossed-coil movement to turn in the opposite direction to swing pointer 104 toward the "maximum" end of the scale. Thus, meter 101 indicates the quotient or ratio $e_p/e_s$, and the generator 15 is tuned to the frequency read on meter 28 at which meter 101 shows the minimum value of such ratio $e_p/e_s$. Of course, if it is desired to tune generator 15 to a maximum reading on meter 101, the connections to the inputs of amplifiers 105 and 106 are reversed, that is, voltage $e_p$ is applied to amplifier 105 and voltage $e_s$ is applied to amplifier 106, so that meter 101 will then indicate the quotient or ratio $e_s/e_p$ which is to be a maximum at the tuned frequency $f_r$.

If desired, the quotient $e_p/e_s$ can also be formed electronically to provide a corresponding D.C. signal which is then displayed by a suitable D.C. meter.

Figure 6:
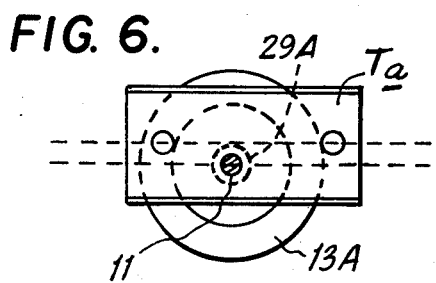
FIG. 6 is a sectional view taken along the line VI—VI on FIG. 5.
Figure 5:
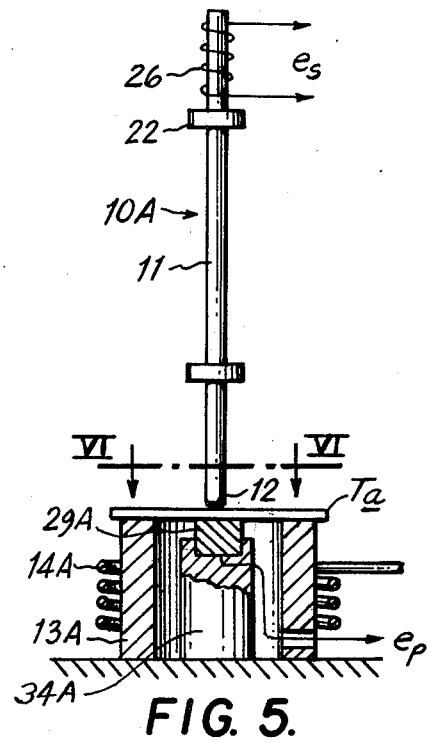

Referring now to FIGS. 5 and 6, it will be seen that a resonant sensing device 10A according to another embodiment of this invention particularly suited for determining the hardness or other surface properties of a test piece $Ta$ constituted by a very thin plate, for example, as in the case of a razor blade, may include a sensor rod 11 similar to the rod 11 of the previously described device 10, and having its contact tip 12 similarly pressed against one surface of the test piece $Ta$. In the device 10A, the test piece $Ta$ is supported on the upper surface of a cylindrical anvil or support 13A formed of a magnetostrictive material and having a winding 14A extending therearound so that the supplying of electrical oscillations to winding 14A, for example, from a variable or tunable generator similar to the generator 15 on FIG. 1, will induce vibrations in the cylindrical anvil 13A for vibrationally exciting the test piece $Ta$ supported thereon. In the resonant sensing device 10A, the amplitude of vibration of test piece $Ta$ is sensed or detected at the surface of the test piece opposed to the surface contacted by tip 12 of sensor rod 11. For example, as shown, device 10A includes an auxliary sensor 29A of piezolectric material which is disposed under the test piece $Ta$ in axial alignment with sensor rod 11 and which is suitably mounted in an insulating support 34A located within the cylindrical anvil 13A. As in the case of the previously described resonant sensing device 10, the pickup coil 26 and the auxiliary sensor 29A may be suitably connected to respective voltmeters for indicating the magnitudes of the respective voltages which correspond to the amplitudes of vibration of sensor rod 11 and of test piece $Ta$ near to the area of contact of tip 12 with the test piece. In order to establish the necessary contact force for holding test piece T$a$ in firm engagement with the cylindrical exciting anvil 13A, the level of the upper surface of auxiliary sensor 29A may be slightly below the level of the upper surface of anvil 13A so that the force urging tip 12 of sensor rod 11 against the test piece, for example, the force of the spring 18 on FIG. 1, will first of all cause the test piece to engage the upper surface of anvil 13A and will further cause some flexing of the test piece into secure contact with auxiliary sensor 29A. Alternatively, in the case where the test piece T$a$ is of a ferromagnetic material, the polarizing current which is supplied to winding 14A in addition to the electrical oscillations will cause a magnetic flux to be produced by which the ferromagnetic test piece is magnetically held in secure engagement with anvil 13A for receiving the vibrational excitation from the latter. It will be understood that the operation of the resonant sensing device 10A in determining the hardness or other surface properties of the test piece T$a$ is the same as that described above with reference to the device 10 of FIG. 1.

Figure 7:
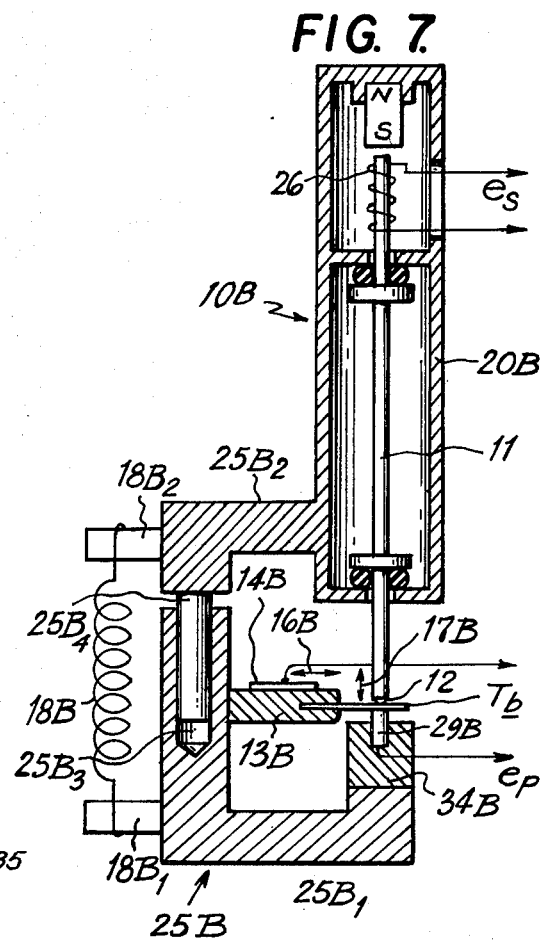
FIG. 7 is a schematic sectional view of a resonant sensing device according to still another embodiment of this invention and which is also particularly suited for indicating the surface properties of plate-like test pieces of small thickness.

Referring now to FIG. 7, it will be seen that the resonant sensing device 10B according to this invention, as there shown, is also intended particularly for use with a relatively small and thin test piece T$b$, and comprises a generally C-shaped frame 25B. The frame 25B is made up of a generally L-shaped lower portion 25B$_1$ having a bore or socket 25B$_3$ in its vertically directed leg, and an upper portion or arm 25B$_2$ having a rod or pin 25B$_4$ depending from one end and being slidably received in bore 25B$_3$ with suitable anti-friction bearings therebetween (not shown) so that arm 25B$_2$ is movable vertically relative to the lower portion 25B$_1$ of the frame. A vise or clamp 13B extends horizontally from the vertical leg of lower frame portion 25B$_1$ and is suitably arranged to clamp or secure the test piece T$b$ at one end of the latter. A slab 14B of a piezoelectric ceramic material is bonded to the upper surface of clamp 13B and is suitably connected to a source of electrical oscillations, for example, the generator 15 of FIG. 1, so that the slab 14B is made to vibrate longitudinally as indicated by the arrow 16B. By reason of the asymmetrical location of the vibrated piezoelectric slab 14B on clamp 13B, flexural vibrations are induced in clamp 13B with the result that the latter vibrates vertically at the portion of the clamp in which test piece T$b$ is secured, as indicated by the arrow 17B. The free end portion of the arm or upper frame portion 25B$_2$ carries a sleeve 20B in which a sensor rod 11 similar to that described above with reference to FIG. 1 is similarly mounted so that the tip 12 at the lower end of sensor rod 11 can be pressed downwardly against the upper surface of the clamped test piece T$b$ by a static force transmitted to the sensor rod from arm 25B$_2$. Such static force may be produced by a tension spring 18B extending vertically between anchor pins 18B$_1$ and 18B$_2$ provided on frame portions 25B$_1$ and 25B$_2$, respectively. As in the embodiment of FIG. 5, the resonant sensing device 10B senses or detects the vibrations of test piece T$b$ at the surface of the latter opposed to the surface contacted by tip 12 of sensor rod 11. Thus, device 10B further includes an auxiliary sensor 29B in the form of a piezoelectric element secured in an insulating member 34B which is mounted on the foot of L-shaped lower frame portion 25B$_1$ so that the static force with which tip 12 is urged against test piece T$b$ may also flex the latter downwardly into intimate contact with the auxiliary sensor element 29B which is axially aligned with sensor rod 11. Of course, the clamp 13B may be made vertically adjustable with respect to lower frame portion 25B$_1$ so that the lower face of the test piece T$b$ can always be made engageable with sensor element 29B.

The resonant sensing device 10B is operated similar to the previously described devices according to this invention, that is, the frequency of the electrical oscillations applied to the piezoelectric slab 14B for effecting vibrational excitation of test piece T$b$ is varied until a maximum or relatively large voltage output from pickup coil 26 on sensor rod 11 indicates that the latter is in a state of resonance, whereupon the frequency of excitation of the test piece is further varied so as to determine that frequency at which the output voltage from the auxiliary sensor element 29B approaches zero or is at least a minimum value, with the frequency thus determined being employed for measuring the hardness or other surface properties of the test piece in comparison with either the resonance frequency of sensor rod 11 in its free state or a similarly determined frequency derived with a standard test piece of known hardness.

When the test piece is of elongated configuration, for example, in the form of a rod, shaft or wire, a resonant sensing device of the type identified generally at 10C on FIG. 8 may be employed, As shown, the resonant sensing device 10C generally comprises a sensor rod 11 similar to that described with reference to FIG. 1 and being similarly mounted in a structure having its parts identified by the same reference numerals so that sensor rod 11 is urged axially by spring 18 relative to the outer housing 19 so as to have its tip 12 pressed against an adjacent end face of an elongated test piece T$c$. In the device 10C, the auxiliary sensor 29C for sensing or detecting the vibrations of test piece T$c$ near to the area of contact of the latter with tip 12 is comprised of a suitably constructed clamp or vise body 36 which is fixed relative to the outer housing 19 of the structure supporting sensor rod 11, as indicated schematically at 25C, and which extends around test piece T$c$ adjacent the end face of the latter engaged by contact tip 12. The clamp or vise body 36 has jaws lined with elements 37 of piezoelectric material which are held in tight frictional engagement with the peripheral surface of test piece T$c$ adjacent the end face of the latter so as to resist or prevent relative sliding movement of the peripheral surface of the test piece and the piezoelectric elements 37 engaged therewith. In order to effect longitudinal vibrational excitation of test piece T$c$, device 10C includes a magnetostrictive tubular clamping body 13C which is in clamping engagement, as at 38, with the peripheral surface of elongated test piece T$c$ at a predetermined axial distance D from the location on the test piece where the elements 37 of auxiliary sensor 29C engage the test piece. A winding 14C extends around the magnetostrictive clamping body 13C and receives electrical oscillations, for example, from the variable frequency generator 15 of FIG. 1.

It will be apparent that the supplying of electrical oscillations to winding 14C will induce vibrations in body 13C so as to effect longitudinal vibration of test piece T$c$, as indicated by the arrow 17C, at the location on the test piece where the magnetostrictive clamping body 13C is secured thereto. Although the distance D is not critical, such distance is preferably selected so that optimal vibrations will occur in the longitudinal direction of the test piece at the end of the latter on which auxiliary sensor 29C is clamped. The resonant sensing device 10C is operated in the same manner as the previously described devices according to this invention, that is, the frequency of the electrical oscillations supplied to winding 14C is varied until a maximum or relatively large output voltage from pickup coil 26 on sensor rod 11 indicates that the latter is in a state of resonance, whereupon the exciting frequency is further varied until the output voltage from the piezoelectric elements 37 of auxiliary sensor 29C indicates that the amplitude of the vibrations of the test piece adjacent the end face thereof contacted by tip 12 has approached zero or attained a minimum value, with the excitation frequency thus determined being a measure of the hardness of test piece $Tc$ when compared with either the resonance frequency of sensor rod 11 in its free state or with a similarly determined frequency obtained with a test piece of known hardness or surface properties.

In all of the previously described embodiments of the invention, the vibrational excitation of the test piece has been effected by inducing vibrations in a member 13, 13A, 13B or 13C which is engaged with the test piece so as to transmit such vibrations to the test piece. However, in certain cases, the vibrational excitation of the test piece can be effected by inducing vibrations directly in the test piece. For example, in the resonant sensing device $10C_1$ of FIG. 9 which is otherwise similar to the resonant sensing device 10C, the test piece $Tc_1$ is assumed to be of a magnetostrictive material and, in that case, vibrations can be directly induced in the test piece by supplying the electrical oscillations to a winding $14C_1$ which extends around the test piece. Similarly, and as shown on FIG. 10, in the event that the test piece $Tc_2$ is of an electrostrictive material, for example, a piezoelectric material, the resonant sensing device $10C_2$ according to this invention may include conductors or leads $14C_2$ extending from the source of electrical oscillations, for example, the variable frequency generator 15 of FIG. 1, to spaced apart locations along the test piece so that the electrical oscillations will cause vibrations to be directly induced in the test piece. Further, as shown on FIG. 11, which shows a modification 10D of the resonant sensing device 10 of FIG. 1, in the case where the test piece $Td$ is of a ferromagnetic material, such test piece may be supported on a passive anvil or base 13D on which a core $14D_1$ of ferromagnetic material, for example, ferrite, is mounted so that the upper end of such core is spaced a small distance from the underside of the test piece below the area of contact of the latter with the tip 12 of sensor rod 11. A coil $14D_2$ extends around core $14D_1$, and is connected to the generator 15 of FIG. 1 so that the oscillations generated by the latter will produce an alternating magnetic field which effects the desired vibrations of the ferromagnetic test piece $T_d$.

Figure 12:
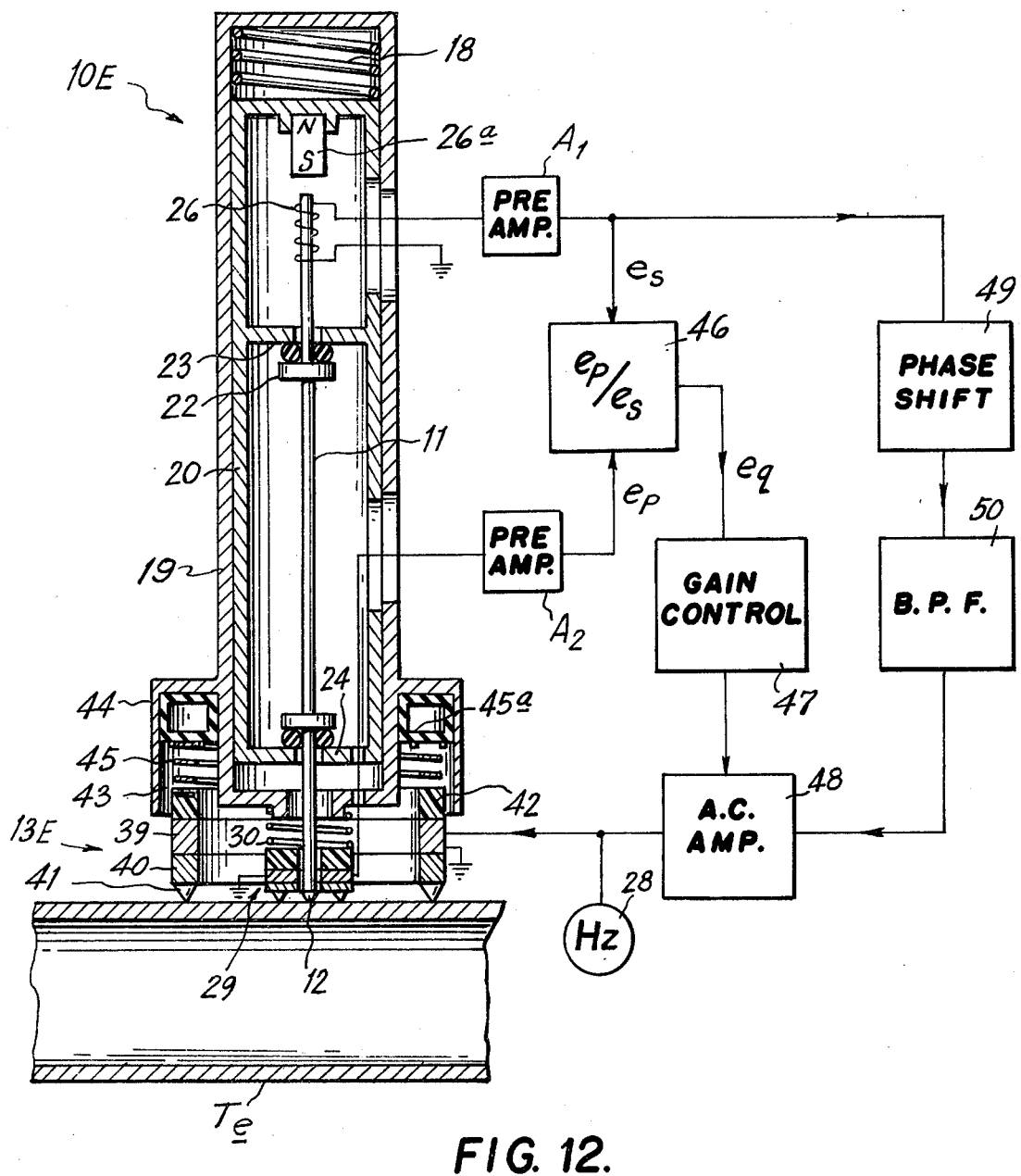
FIG. 12 is a schematic axial sectional view of a resonant sensing device according to still another embodiment of this invention for use with test pieces of varying shapes and thicknesses and which is particularly suited for indicating the surface properties of tubes or other hollow bodies.

In each of the previously described embodiments of this invention, the test piece was vibrationally excited at a surface of the latter other than the surface contacted by the tip 12 of the sensor rod 11. However, certain test pieces, for example, hollow tubes, can only be engaged at the outer surface thereof and, in that case, the resonant sensing device 10E of FIG. 12 may be employed for determining the hardness or other surface properties of the test piece. Such device 10E is shown to generally comprise a sensor rod 11 and auxiliary sensor 29 similar to the correspondingly numbered elements described with reference to FIG. 1, and being similarly urged against the outer surface of the tubular test piece $Te$. However, in the device 10E the exciting means 13E for effecting vibration of the test piece is of annular configuration and extends coaxially around the annular auxiliary sensor 29. As shown, the exciting means 13E may include a ring 39 of piezoelectric material bonded between a lower metal ring 40 having contact points 41 depending therefrom and an upper insulating ring 42 through which a downward force is applied to the exciting means 13E for holding the contact points 41 firmly against the outer surface of the tubular test piece. In the device 10E, as shown, the insulating ring 42 is axially movable in an annular space 43 defined between the housing 19 and a jacket 44 spaced radially from the latter, and a coil spring 45 of rectangular cross-section for additional lateral stability is disposed within the annular space 43 and has its lower end anchored in ring 42 downwardly on ring 42 and thereby provide the force for maintaining engagement of the contact points 41 with test piece $Te$. The vibrations produced by exciting means 13E are isolated from sensor rod 11 and from auxiliary transducer 29 by radially spacing exciting means 13E from housing 19 and jacket 44, as shown, and by providing a hollow ring 45a of acoustically soft material as a seat for the upper end of spring 45. In order to provide vibrational excitation of the test piece, electrical oscillations are applied to the piezoelectric ring 39 for inducing vibrations in the latter which are transmitted through lower ring 40 and contact points 41 to the test piece at the outer surface of the latter. Simultaneously, pickup coil 26 and auxiliary sensor 29 are respectively effective to sense or detect the amplitude of vibration of sensor rod 11 and the amplitude of vibration of the test piece near to the area of contact of the latter with tip 12 of the sensor rod, as in the previously described embodiments.

In all of the previously described embodiments of this invention, the source of the electrical oscillations for effecting vibrational excitation of the test piece has been described as being a manually tunable generator. However, any of the previously described devices 10, 10A, 10B and 10C, as well as the device 10E of FIG. 12, may be provided with an automatic tuning arrangement by which the frequency of the vibrational excitation of the test piece is automatically tuned to the frequency at which the ratio of the voltage output from the auxiliary sensor 29 or the like to the voltage output from the pickup coil 26 is zero or at least a minimum value. For example, as shown schematically on FIG. 12, such an automatic tuning arrangement may include a function generating circuit 46 which receives the output voltages $e_p$ and $e_s$ from pre-amplifiers $A_2$ and $A_1$ connected with auxiliary sensor 29 and pickup coil 26, respectively, and provides a DC control voltage $e_q$ which is proportional to the ratio $e_p/e_s$. Such control voltage $e_q$ is applied to a gain control circuit 47 for controlling the gain of an amplifier 48. The AC output of pickup coil 26 which, of course, has a frequency corresponding to that at which sensor rod 11 is being vibrated, is also applied through a phase shifting circuit 49 and a band pass filter 50 to the input of amplifier 48, while the output of amplifier 48 is applied to the piezoelectric ring 39 of the exciting means 13E and also to the frequency meter 28. The function generating circuit 46 and gain control circuit 47 are arranged so that the gain of amplifier 48 will be high when the ratio $e_p/e_s$ is small, and vice versa, so that the system will be in a state of self-excitation only at the frequency within the pass band of filter 50 for which the ratio $e_p/e_s$ has a minimum value. That frequency is the one which is read on meter 28 to indicate the hardness or other surface properties of the test piece in comparison with either the resonance frequency of sensor rod 11 in its free state or with a similarly determined frequency obtained when the device 10E is employed with a test piece of known hardness.

In all of the previously described embodiments of the invention, the vibrational excitation of the test piece has been effected at a location on the latter substantially spaced from the location on the test piece at which the latter is engaged by the contact tip 12 of the sensor rod 11. However, as shown on FIG. 13 a resonant sensing device 10F in accordance with this invention may be provided to effect vibrational excitation of the test piece Tf at a location on the surface of the latter opposite to that engaged by contact tip 12, which location is axially aligned with sensor rod 11. More specifically, it will be seen that, in the device 10F, the sensor rod 11 and auxiliary sensor 29 are similar to the correspondingly numbered elements described with reference to FIG. 1 and are similarly mounted so as to be engageable with the same surface of the test piece, while the exciting means 13F acts against the opposite surface of test piece Tf in axial alignment with sensor rod 11. In the illustrated embodiment, the exciting means 13F is shown to be constituted by an elongated rod 51 of magnetostrictive material having flanges 52 spaced apart at nodes of the rod intermediate its ends and at which rod 51 can be supported and urged axially, in a manner similar to sensor rod 11, so as to firmly press one end of rod 51 against the underlying surface of the test piece. A winding 53 is provided around the magnetostrictive exciting rod 51 and is adapted to receive electrical oscillations, for example, from the variable frequency generator 15, so that longitudinal vibrations are induced in exciting rod 51 and transmitted to the test piece Tf at the location of the engagement of the end of rod 51 with the undersurface of the test piece.

It will be apparent that the device 10F of FIG. 13 may be operated similarly to the device of FIG. 1, that is, the frequency of the electrical oscillations from generator 15 may be varied until meter 27 indicated that sensor rod 11 is in a state of resonance, whereupon the frequency of the electrical oscillations is further varied, while rod 11 remains in the state of resonance, until meter 35 indicates that auxiliary sensor 29 has detected the minimum amplitude of vibration of test piece Tf at the region near to its area of contact with tip 12 of sensor rod 11. The frequency of the electrical oscillations resulting in the foregoing condition is read on meter 28 so as to indicate the hardness or other surface properties of the test piece in comparison with either the free resonance frequency of rod 11 or a similarly determined frequency for a test piece of known hardness.

The device 10F of FIG. 13 is advantageous in that, by the provision of simple switching means, the exciting means 13F can be made to function as the resonant sensor rod, the sensor rod 11 and its pickup coil 26 can be made to function as the auxiliary sensor, and the auxiliary sensor 29 can be made to function as the exciting means. More specifically, as shown, switches $SW_1$ and $SW_2$ can be provided so that, when such switches are in the position shown in full lines on FIG. 13, piezoelectric ring 33 of auxiliary sensor 29 is connected through switch $SW_1$ to voltmeter 35 while winding 53 on rod 51 is connected through switch $SW_2$ to generator 15. It will be apparent that, with switches $SW_1$ and $SW_2$ in such positions shown in full lines, the electrical oscillations received by winding 53 from generator 15 induce vibrations in rod 51 which are transmitted to test piece Tf while voltmeters 27 and 35 respectively indicate the amplitude of vibration of sensor rod 11 and the amplitude of vibrations of the test piece near to the area of contact of sensor rod tip 12 with the test piece. However, when switches $SW_1$ and $SW_2$ are simultaneously changed over to the position shown in broken lines on FIG. 13, piezoelectric ring 33 is connected to generator 15 for receiving the electrical oscillations from the latter and thereby imparting vibrational excitation to the test piece, while winding 53 on rod 51 is connected through switch $SW_2$ to voltmeter 35 so that the latter will then indicate the amplitude of vibration of rod 51. In the case where the rod 51 is to function as the sensor rod, the end thereof pressed against the underside of the test piece is provided with a contact tip 54 of a configuration similar to that described above with respect to the tip 12 on rod 11.

It will be apparent that, with switches $SW_1$ and $SW_2$ in the positions shown in broken lines, generator 15 is tuned until voltmeter 35 indicates a maximum voltage corresponding to a state of resonance of the rod 51, whereupon generator 15 is further tuned until voltmeter 27 provides a zero or minimum reading indicating that the amplitude of vibration of the test piece, as then detected by the rod 11 and its tip 12, is zero or at least a minimum value. It will be appreciated that, as a consequence of the switches $SW_1$ and $SW_2$ provided in the device 10F, the switches can be manipulated to measure the hardness or other surface properties of the test piece Tf at the opposite surfaces of the test piece without relocating the test piece relative to the device 10F.

It will be appreciated that, in all of the above described devices embodying this invention, the exciting means for effecting vibrational excitation of the test piece, for example, the anvil 13 on FIG. 1, and the auxiliary sensor for detecting the amplitude of vibration of the test piece at a location near to the area of contact of the latter with the tip 12 of the sensor rod 11 are dimensioned and arranged to have resonant frequencies that are substantially different from the resonance frequency of the sensor rod 11 for which the exciting electrical oscillations are tuned either manually or automatically when measuring the hardness or other surface properties of a test piece.

In all of the above described embodiments of the invention, the mechanical resonating means or sensor has been in the form of a rod 11 of magnetostrictive material in which longitudinal vibrations are produced to generate the voltage or signal $e_s$ in pickup coil 26 extending around such rod. However, such mechanical resonating means may have other configurations and other modes of vibration, for example, so as to be flexurally vibrated, and other types of pickup, for example, electrodynamic, eddy-current, electromagnetic, electrostatic or electrooptical pickups, may be employed for detecting the amplitude of vibration of such mechanical resonating means. Similarly, many different types of pickups can be employed for detecting the amplitude of vibration of the test piece near to the area of contact of the latter with the tip 12 of the mechanical resonating means.

Further, in all of the above specifically described and illustrated embodiments of the invention, the force with which the tip 12 of mechanical resonating means 11 is held against the test piece is maintained constant, as is the free resonance frequency of the mechanical resonating means or sensor rod 11, and the frequency of the vibratory excitation of the test piece is varied to determine that frequency at which the amplitude of vibration of the test piece near to the area of contact with the tip 12 is reduced to a minimum value while the sensor rod 11 or other mechanical resonating means is in a state of resonance as indicated by a relatively large amplitude of vibration of the sensor rod, with the difference between the frequency thus determined and the resonance frequency in its free state being a measure of the hardness or other surface properties of the test piece. However, other modes of operation of the apparatus according to this invention may be employed.

For example, in a manner similar to that disclosed in U.S. Pat. No. 3,153,338, the frequency at which the test piece is vibrated may be fixed at a value different from the resonance frequency of the sensor rod 11 or other mechanical resonating means in the free state or condition of the latter, and the static force by which the sensor rod tip 12 is held in steady contact with the vibrated test piece is progressively increased until the amplitude of vibration of the test piece near to the area of contact with tip 12 is a minimum value while the amplitude of vibration of the sensor rod 11 is relatively large. In this mode of operation, the magnitude of the static contact force required to achieve the foregoing conditions is measured as an indication of the hardness or other surface properties of the test piece.

In another mode of operating a resonant sensing device according to this invention, which operating mode is generally similar to that disclosed in U.S. Pat. No. 3,572,097, both the frequency of excitation of the test piece and the static force with which the contact tip 12 on sensor rod 11 is held against the test piece are fixed, and a characteristic or parameter of the sensor rod 11 or other mechanical resonating means which determines its resonance frequency is varied until the measured amplitude of vibration of the test piece is a minimum value while the measured or detected amplitude of vibration of the sensor rod is a relatively large value, with the variation of such characteristic or parameter from the value thereof for the resonance state of the sensor rod in its free condition being an indication of the hardness or other surface properties of the test piece. Among the resonance frequency determining characteristics or parameters of the mechanical resonating means that may be varied are an elastic modulus thereof, as by varying a magnetic polarizing field in the case where the mechanical resonating means includes a magnetostrictive rod or an electric polarizing field in the case where the mechanical resonating means includes an electrostrictive or piezoelectric rod, or by varying the temperature of the mechanical resonating means. The varied characteristic or parameter of the mechanical resonating means which determines its resonance frequency may also be its shape, mass distribution relative to its nodes and loops of vibration, or a force other than the static contact force which is applied to the mechanical resonating means remote from its contact surface to add elastic strain energy.

Although illustrative embodiments of this invention have been described in detail herein with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. The method of determining the surface properties of a test piece comprising holding a mechanical resonating means against a surface of the test piece with a static force sufficient to maintain steady contact with the test piece at a contact surface shaped to provide increasing areas of contact with increasing deformation of the test piece surface by the shaped contact surface, exciting the test piece into vibration with a frequency which is varied to cause said mechanical resonating means to attain a state of resonance in dependence on the mechanical coupling between said mechanical resonating means and the test piece at said area of contact therebetween, measuring the amplitude of vibration of the vibrated test piece at a region of the latter which is adjacent to, and outside of said area of contact of the test piece with the mechanical resonating means, measuring the amplitude of vibration of said mechanical resonating means so as to ascertain when the latter is in said state of resonance, and further varying the frequency of the vibratory excitation of the test piece in a range within which said mechanical resonating means remains in said state of resonance to determine that frequency at which the measured amplitude of vibration has a minimum value so that the difference between the frequency thus determined and the resonance frequency of said mechanical resonating means when free of the test piece is an indication of the surface properties of the test piece.

2. The method according to claim 1; in which said region of the test piece at which the amplitude of vibration thereof is measured is spaced from the area of contact of said mechanical resonating means with the test piece by a distance at least ten times the mean radius of the area of contact of said test piece surface with said shaped contact surface.

3. The method according to claim 2; in which said distance is less than one-quarter of the wavelength of the vibrations which are excited in said test piece.

4. The method according to claim 1; in which the determined frequency is that at which there is obtained the minimum ratio of the measured amplitude of vibration of the test piece to the measured amplitude of vibration of the mechanical resonating means.

5. The method according to claim 1; in which the determined frequency is that at which there is obtained the maximum ratio of the measured amplitude of vibration of the mechanical resonating means to the measured amplitude of vibration of the test piece.

6. The method according to claim 1 in which the test piece excitation is effected so as to provide the vibration thereof, at least in the vicinity of said area of contact, with a substantial component in the direction of greatest sensitivity of said mechanical resonating means, and said measuring of the amplitude of vibration of the test piece is effected in said direction of said component.

7. A device for indicating the surface properties of a test piece, comprising mechanical resonating means having a predetermined resonance frequency in its free state and including a contact surface with progressively increasing cross-sectional areas, means for holding said contact surface in steady indenting contact against a surface of the test piece so as to provide increasing areas of contact therebetween with increasing deformation of said surface of the test piece by said contact surface, means for exciting the test piece into vibration with a frequency at which said mechanical resonating means is adapted to attain a state of resonance in dependence on the mechanical coupling between said mechanical resonating means and the test piece at the area of contact therebetween, first detecting means for detecting the amplitude of vibration of the test piece at a region of the latter which is adjacent to, and outside of said area of contact of said mechanical resonating means with the test piece, and second detecting means for detecting the amplitude of vibration of said mechanical resonating means.

8. A device according to claim 7; further comprising means connected with said first and second detecting means for establishing a ratio of said amplitude of vibration of the test piece and said amplitude of vibration of the mechanical resonating means.

9. A device for indicating the surface properties of a test piece, comprising mechanical resonating means having a predetermined resonance frequency in its free state and including a contact surface with progressively increasing cross-sectional areas, means for holding said contact surface in steady indenting contact against a surface of the test piece so as to provide increasing areas of contact therebetween with increasing deformation of said surface of the test piece by said contact surface, means for exciting the test piece into vibration with a variable frequency which is selected to cause said mechanical resonating means to attain a state of resonance in dependence on the mechanical coupling between said mechanical resonating means and the test piece at the area of contact therebetween, means operatively associated with said mechanical resonating means for indicating the amplitude of vibration of the latter and thereby establishing when said mechanical resonating means is in said state of resonance, and means for indicating the amplitude of vibration of the test piece at a region of the latter which is adjacent to, and outside of said area of contact of said mechanical resonating means with the test piece so that the frequency of the vibratory excitation of the test piece can be further varied in a range within which said mechanical resonating means remains in said state of resonance to determine that frequency at which the indicated amplitude of vibration of the test piece has a minimum value with the difference between the frequency thus determined and said predetermined resonance frequency of the mechanical resonating means in its free state being an indication of the surface properties of the test piece.

10. A device according to claim 9; further comprising means coupled with said means for indicating the amplitude of vibration of the test piece and said means for indicating the amplitude of vibration of said mechanical resonating means and being operative to indicate the ratio of said amplitudes of vibration of said test piece and said mechanical resonating means, respectively.

11. A device according to claim 9; in which said mechanical resonating means includes an elongated sensor rod having said contact surface at an end thereof.

12. A device according to claim 11, in which said means for indicating the amplitude of vibration of the test piece includes an annular auxiliary sensor arranged coaxially about said sensor rod and engageable with the same surface of the test piece as said contact surface on the end of the sensor rod.

13. A device according to claim 11, in which said means for indicating the amplitude of vibration of the test piece includes an auxiliary sensor engageable with a surface of the test piece opposed to said surface of the latter contacted by said contact surface on the sensor rod and being axially aligned with the latter.

14. A device according to claim 11; in which the test piece is of elongated configuration, said surface of the test piece against which said contact surface of the sensor rod is held is at one end of the elongated test piece, and said means for indicating the amplitude of vibration of the test piece extends around the latter adjacent said one end surface of the test piece.

15. A device according to claim 14; in which said means for indicating the amplitude of vibration of the test piece includes at least one piezo-electric element clampled to said elongated test piece adjacent said one end surface of the latter.

16. A device according to claim 9; in which the test piece is of a magnetostrictive material, and said means for exciting the test piece into vibration includes a driving coil operatively associated with the magnetostrictive test piece and electrical oscillation generating means connected with said coil to cause the latter to produce an alternating magnetic field by which the test piece is vibrated.

17. A device according to claim 9; in which said test piece is of an electrostrictive material, and said means for exciting the test piece into vibration includes electrical oscillation generating means connected with said electrostrictive test piece for producing an alternating electric field in the test piece by which the latter is vibrated.

18. A device according to claim 9; in which said test piece is of a ferromagnetic material, and said means for exciting the test piece into vibration includes electromagnetic means positioned adjacent said test piece and out of contact with the latter for producing an alternating magnetic field by which the ferromagnetic test piece is vibrated.

19. A device according to claim 9; in which said means for exciting the test piece into vibration includes a support for the test piece, and electrically energized means for generating vibrations in said support to be transmitted to the test piece.

20. A device according to claim 9; in which said means for exciting the test piece into vibration includes an exciting probe engageable with the test piece, and electrically energizable means for generating vibration in said probe to be transmitted to the test piece engaged therewith.

21. A device according to claim 20; in which said mechanical resonating means includes an elongated sensor rod having said contact surface at an end thereof, and said exciting probe is annular and arranged coaxially about said sensor rod for engaging said test piece at the same surface of the latter as is contacted by said contact surface on the sensor rod.

22. A device according to claim 20; in which said contact surface of the mechanical resonating means and said exciting probe are in axial alignment with each other and respectively engageable with opposed surfaces of the test piece.

* * * * *